(12) United States Patent
Tremolada et al.

(10) Patent No.: US 10,689,623 B2
(45) Date of Patent: Jun. 23, 2020

(54) METHOD AND DEVICE FOR PREPARING NON-EMBRYONIC STEM CELLS

(71) Applicant: LIPOGEMS INTERNATIONAL S.P.A., Milan (IT)

(72) Inventors: Carlo Tremolada, Milan (IT); Carlo Ventura, Bologna (IT); Milford Graves, Jamaica, NY (US)

(73) Assignee: LIPOGEMS INTERNATIONAL S.P.A., Milan (IT)

( * ) Notice: Subject to any disclaimer, the term of this patent is extended or adjusted under 35 U.S.C. 154(b) by 0 days.

(21) Appl. No.: 15/703,564

(22) Filed: Sep. 13, 2017

(65) Prior Publication Data

US 2018/0066232 A1 Mar. 8, 2018

Related U.S. Application Data

(62) Division of application No. 14/415,579, filed as application No. PCT/IB2013/055989 on Jul. 22, 2013.

(30) Foreign Application Priority Data

Jul. 23, 2012 (IT) .............................. GE2012A0073

(51) Int. Cl.
| | |
|---|---|
| *C12N 5/0775* | (2010.01) |
| *C12M 1/42* | (2006.01) |
| *A61H 23/00* | (2006.01) |
| *C12N 13/00* | (2006.01) |
| *A61B 17/00* | (2006.01) |

(52) U.S. Cl.
CPC .......... *C12N 5/0667* (2013.01); *A61H 23/00* (2013.01); *C12M 35/04* (2013.01); *C12N 13/00* (2013.01); *A61B 2017/00969* (2013.01); *C12N 2527/00* (2013.01)

(58) Field of Classification Search
CPC .... C12N 5/0653; C12N 5/0667; C12N 13/00; C12M 35/04
See application file for complete search history.

(56) References Cited

U.S. PATENT DOCUMENTS

| 3,951,140 A | 4/1976 | Eggleton et al. |
|---|---|---|
| 2007/0293893 A1 | 12/2007 | Stolen et al. |
| 2007/0299539 A1 | 12/2007 | Othman et al. |
| 2008/0195007 A1 | 8/2008 | Podrazhansky et al. |
| 2013/0123747 A1 | 5/2013 | Tremolada |

FOREIGN PATENT DOCUMENTS

| WO | 2011/145075 A2 | 11/2011 |
|---|---|---|
| WO | 2011/158845 A1 | 12/2011 |

OTHER PUBLICATIONS

Feng et al., "Molecules that Promote or Enhance Reprogramming of Somatic Cells to Induced Pluripotent Stem Cells", Cell Stem Cell, 4, Apr. 3, 2009, p. 301-312.*
Robinton et al., "The promise of induced pluripotent stem cells in research and therapy", Nature, Jan. 19, 2012, vol. 481, p. 295-305.*
Database WPI, Week 200835, Thomson Scientific, London, GB, AN 2008-F06537 & CN201035807Y (Yang, J), Mar. 12, 2008.
Tong Z et al, Vocal fold-mimetic environment for fibroblastic differentiation of mesenchymal stem cell, 38th Annual Northeast Bioengineering Conference, NEBEC 2012—NEBEC 20122012, IEEE Computer Society, Jan. 1, 2012, pp. 410-411, ISBN: 978-1-4673-1141-0.
Tirkkonen L et al, The effects of vibration loading on adipose stemcell number, viability and differentiation toward-bone-forming cells, Journal of the Royal Society, Interface, The Royal Society, London, GB, vol. 8, No. 65, Dec. 7, 2011, pp. 1736-1747, ISSN: 1742-5689, DOI: 10.1098/RSIF.2011.0211.

* cited by examiner

*Primary Examiner* — Ruth A Davis
(74) *Attorney, Agent, or Firm* — Jeffrey N. Townes; Cozen O'Connor

(57) ABSTRACT

The invention relates to a process for preparing a non-expanded tissue derivative, that is not subjected to cell proliferation in vitro, comprising a vascular-stromal fraction enriched in stem and multipotent elements, such as pericytes and/or mesenchymal stem cells, or for preparing non-embryonic stem cells obtained from a tissue sample or from said derivative, wherein said tissue derivatives or said cells are subjected to vibrations derived from a heart sound such to control the degree of differentiation or possible differentiation of said stem and multipotent elements into several other types of cells that is to optimize their potency. The invention relates also to a device for carrying out said process, to stem cells obtainable by the process as well as a drug for the regeneration of an animal tissue.

5 Claims, 7 Drawing Sheets

Heart sound signal

METHOD AND DEVICE FOR PREPARING NON-EMBRYONIC STEM CELLS

CROSS-REFERENCE TO RELATED APPLICATIONS

This application is a Divisional of U.S. patent application Ser. No. 14/415,579, filed Jan. 17, 2015, which is a national-stage application under 35 U.S.C. § 371 of International PCT Application No. PCT/IB2013/055989, filed Jul. 22, 2013, which claims priority to Italian Patent Application No. GE2012A000073, filed Jul. 23, 2012, all of which are incorporated herein by reference in their entirety.

The invention relates to a process and a device for preparing a non-expanded tissue derivative comprising a vascular-stromal fraction enriched in stem and multipotent elements, such as pericytes and/or mesenchymal stem cells, or for preparing non-embryonic stem cells obtained from said derivative or from a tissue sample, particularly an adipose one.

In the last years the basic research in the medicine field has faced a real revolution about how to study and treat diseases. This is essentially due to the goals achieved in the genetic engineering field and to the increasingly deep knowledge about stem cells.

Stem cells are primitive unspecialized cells having the ability to transform into other different types of cells through a process called cell differentiation. The ability of each stem cell to differentiate into another cell is defined as "potency".

Specifically the totipotency is the ability of a single cell to divide and to produce all of the differentiated cells in an organism, including extra-embryonic tissues. This is the case of zygotes.

On the contrary pluripotency is the ability of a single cell to divide and to differentiate into any cell derived from one of the three germ layers: mesoderm (muscles, bones, cartilage, blood), endoderm (interior lining of the stomach, of the gastrointestinal tract), ectoderm (epidermal tissues and nervous system). Pluripotent cells derive from embryos.

Non-embryonic stem cells, called also adult stem cells, are the so called multipotent cells since they have the potential to differentiate in a limited number of other cells. Their main role is to maintain and repair tissues where they are located. For example hematopoietic stem cells can develop in any blood cell, but they cannot differentiate into cells of other type such as those of the nervous system such as it occurs, on the contrary, in the case of pluripotent stem cells.

Due to their characteristic to be transformed in any other type of cell, and therefore to potentially repair any type of damaged tissue, it is clear how pluripotent stem cells are of great interest to the worldwide scientific community.

On the other hand, since pluripotent stem cells can be obtained only by destroying the embryo from which they derive, there are important ethical problems that prevent them from being fully employed. For this reasons clinical researches in the last years have been directed towards the so called induced pluripotent stem cells (iPSCs).

In practice these are adult stem cells, such as for example those of the skin, blood, hair, or even any type of non-stem adult somatic cells, such as for example skin fibroblasts, which are reprogrammed in order to behave like pluripotent cells. Such "reprogramming" occurs by inserting in the genome, by the genetic engineering, some genes that allow basic cells to acquire the capacity to differentiate into different types of tissue similarly to what occurs for the embryonic stem cells. To this end see for example the studies made by Whitehead Institute for Biomedical Research, Cambridge, Mass. and by the University of Kyoto published by the magazine Science Express in 2007.

The genetic reprogramming operation however is not at all simple and it is still well away from a possible use in the routine clinical practice.

Therefore the aim of the present invention is a process for preparing pluripotent stem cells or, however, having an optimized potency, starting from adult cells without using complex and expensive genetic engineering techniques.

The invention achieves the aim by means of an unexpected discover made by the inventor.

It is known that specific external factors can influence the development of the fetus and the consequent formation of the organs. For example think of all those environmental factors that can induce genetic mutations such as for example the consumption of specific drugs by the mother in pregnancy or the exposure to ionizing radiations or to teratogen chemical/physical elements. It is reasonable to suppose that possible vibrations can cause specific cells to change or anyway to direct their development in specific directions than other ones. There are different scientific papers that point out how the music, for example, can affect the metabolism of living beings.

On the other hand since the first morphogenetic event in any embryonic species is the cardiogenesis, and the heart, or anyway what will be later a mature heart, is an organ characterized by a continuous pulsation, the sounds and/or vibrations which are necessarily produced by such pulsation are an aspect that is and that will be always present during the development of embryonic cells and during all the life. Suffice to think that the cardiogenesis in the human being begins already from the seventh day of life of the embryo.

From what stated above derives the idea of the inventor: the heart sound does not affect only the cardio/vasculo-genesis and therefore the differentiation of the mesoderm, but also the development of other cells acting like an orchestrating function for all the living organisms with the tissues that maintain a kind of memory/signature of the heart vibrations that have followed the embryonic development. Therefore it is possible to use the heart sound to bring the adult stem cells back to a state having characteristics similar to the embryonic state namely in order to optimize the potency thereof.

To this end the invention provides to prepare a non-expanded tissue derivative namely not subjected to cell proliferation in vitro, comprising a vascular-stromal fraction enriched in stem and multipotent elements, such as pericytes and/or mesenchymal stem cells, or to prepare non-embryonic stem cells obtained from a tissue sample, particularly adipose one, or from said derivative, by subjecting said tissue derivatives or said cells to vibrations derived from a heart sound. Particularly said vibrations are induced through acoustic waves obtained from one or more heart sounds within one or more cardiac cycles of the individual from whom the tissue sample has been taken, or any other individual, even belonging to a different species, and repeated throughout the process length.

Said vibrations allow the degree of differentiation or possible differentiation of said stem and multipotent elements in different other types of cells to be controlled that is they allow the potency of said stem and multipotent elements to be optimized.

Non-expanded tissue derivative means an aggregate of cells of the tissue taken from the patient, which is not cultured and therefore cell elements (stem and non-stem ones) contained therein are not cultured in vitro into a culture medium, that is they are not subjected to proliferation (called also as expansion) in vitro.

According to one embodiment, the process comprises the step of acquiring by a microphone or the like the sounds generated by the heart, particularly of the individual from whom the tissue sample has been taken, and storing them on an analog or digital medium, possibly sampling the signal acquired in this manner, in order to deliver again said sounds, possibly processed, to the stem cells of the tissue sample. In practice the heart sounds are directly acquired by one or more microphones such as it occurs for example in phonocardiography examinations or auscultations through stethoscope.

As an alternative or in combination it is possible to obtain the heart sounds indirectly by using ultrasonic Doppler flow-metering techniques. To this end, according to one embodiment, the process comprises the step of acquiring the heart sound by ultrasonography examination, particularly of the individual from whom the tissue sample has been taken, extracting the Doppler signal from echoes of ultrasound waves received by soundproofing with a probe the heart, or a part thereof, or a blood vessel.

Stem cells to be treated can be provided inside a non-expanded tissue derivative/product, or they can be extracted therefrom such to be expanded in culture.

Stem cells can also be extracted from a tissue sample.

As a whole, the process can comprise the steps of:

a) preparing a non-expanded tissue derivative from non-enzymatic "minimal manipulation", of the original tissue, as lipoaspirate, said derivative being intended as composed of aggregates of cells of the original tissue, such as adipocytes in case of lipoaspirate, encompassed by a vascular-stromal component containing stem cells and/or multipotent elements such as pericytes and mesenchymal stem cells;

b) as an alternative or in combination to step a), preparing a cell suspension from a tissue sample or from the derivative as of step a), particularly into a $CO_2$ incubator, collecting the stem cells from said cell suspension;

c) subjecting said stem cells of the tissue derivative or obtained from a tissue sample or from the derivative as of step a), to vibrations derived from a heart sound.

The term "minimal manipulation" of cells means that (stem and non-stem) cells are not expanded (cultured and proliferated in vitro in culture) and are not subjected to a series of "treatments" such as enzymatic dissociations and extraction, centrifugations and separations of cell populations, enriching of some cell populations to the detriment of other ones (for example flow cytofluorometry separation) and other similar treatments.

The fact that cells can be subjected to a minimal manipulation allows the process and the product obtained by said process not to fall within the "Drug-major manipulation" regulations.

The tissue sample can advantageously comprise adipose material extracted for example by liposuction/lipoaspiration, and the step b) of the process can provide the adipose material to be enzymatically treated for releasing stem cells after possibly having reduced the adipose tissue into smaller parts.

Therefore the process can be applied both to non-expanded cell aggregates (for example cells obtained by the process described in the patent WO2011/145075), and to cells derived therefrom (and therefore expanded cells) or other types of stem cells and non-stem cells (for example adult somatic cells such as fibroblasts) that should be necessarily isolated and expanded. Said isolated and expanded cells are therefore subjected to a so called "major manipulation" and are considered as ATMPs (Advanced Therapies Medicinal Products) and are subjected to the regulation of cGMPs (current Good Manufacturing Practice).

According to a particular advantageous embodiment, the tissue comprises transplantation adipose tissue obtained from lobular fat material extracted, for example, by liposuction, said fat material being composed of a fluid component comprising an oil component, a hematic component and/or sterile solutions and of a solid component comprising vascular-stromal structures, cell fragments and/or one or more cell macroagglomerates of heterogeneous size and comprising stem cells. The process provides the step of dividing said fat material into cell agglomerates with a smaller size than the size of said macroagglomerates, such that said cell and/or vascular-stromal agglomerates have a size equal to or smaller than a predetermined value, and such that said sizes are on average equal to one another, the step subjecting said cells/agglomerates to vibrations being carried out for all the length of the process or only for a part thereof. As an alternative or in combination with the division step, the process can provide at least one step washing the cell aggregates which is carried out contemporaneously with a step separating the fluid component from the solid component.

According to another aspect the invention relates to stem cells, particularly human adult stem cells (HSCs), which can be obtained by a process mentioned above, as well as to non-stem somatic adult cells (e.g. skin fibroblasts), and to the use thereof for preparing a drug for regenerating an animal tissue, particularly for cell therapy and regenerative medicine in various clinical contexts among which cardiovascular, neurodegenerative, endocrine/metabolic diseases.

According to a further aspect, the invention relates to a device for optimizing the potency of non-embryonic stem cells comprising a reproduction unit configured for reproducing one or more heart sounds and a speaker element connected or connectable to an output of the reproduction unit. The device is provided coupled to a container for collecting a non-expanded tissue derivative containing non-embryonic stem cells or made of non-embryonic stem cells such to subject the cells contained therein to sound waves coming from said speaker element.

The reproduction unit advantageously comprises an input for reading heart sound samples stored into a storage element and a sound processing chain for reconstructing and outputting said heart sounds possibly processed and repeated for the process length.

According to one embodiment the device comprises an acquisition unit able to supply the heart sound samples to the reproduction unit. The acquisition unit comprises a transducer element and a processing chain able to store the heart sounds when said transducer element is placed in contact with or near the heart or a blood vessel of a living being.

The transducer element typically is a microphone, but it can also comprise an ultrasound probe. In this case the acquisition unit comprises an apparatus or a part of an apparatus for ultrasonic Doppler flow-metering able to extract the samples of the audio Doppler signals and to store them on a storage element the reproduction unit having access thereto.

The device according to the invention is not provided only in combination with a container collecting a non-expanded tissue derivative containing non-embryonic stem cells or made of non-embryonic stem cells. The speaker element can be configured like a probe for being coupled directly to the body of a patient in order to induce vibrations directly to the stem cells provided in his/her tissues.

Further characteristics and improvements are object of the subclaims.

Characteristics of the invention and advantages deriving therefrom will be more clear from the following detailed description of the annexed figures, wherein.

Figure 7:
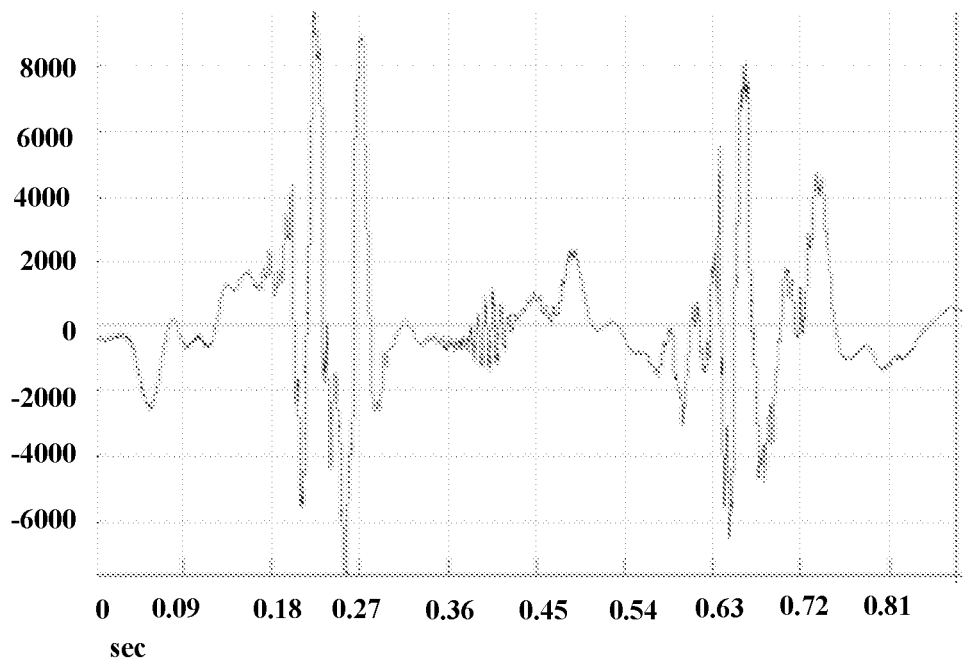
Figure 8:
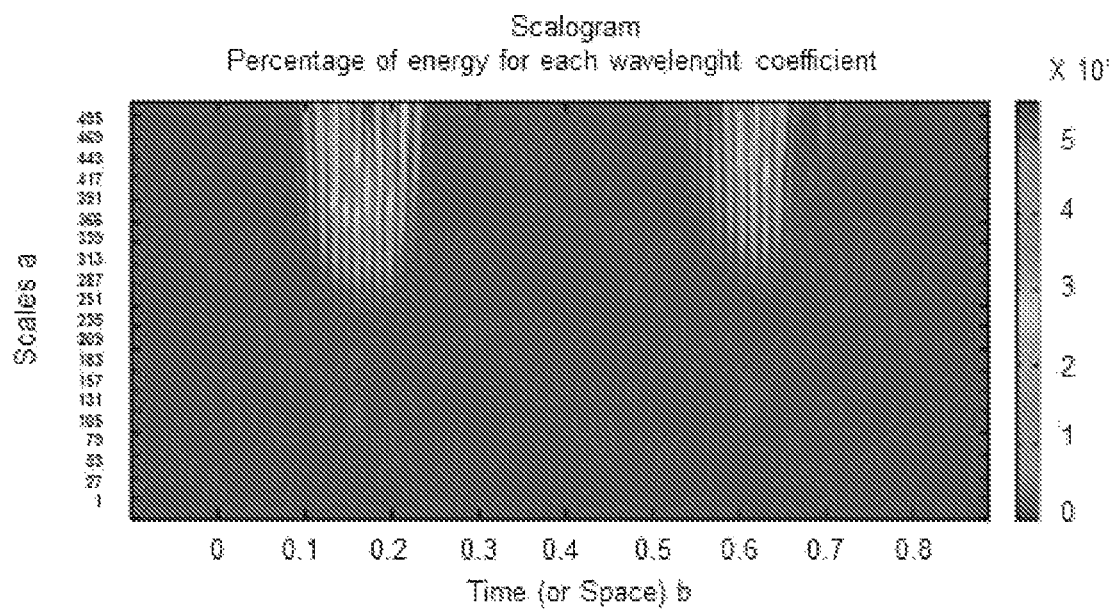

FIGS. 7 and 8 (from M. Vishwanath Shervegar, Ganesh.V.Bhat, Raghavendra M Shetty K. Phonocardiography—the future of cardiac Auscultation. International Journal of Scientific & Engineering Research Volume 2, Issue 10, October 2011, pp 1-12; http://www.ijser.org) are an example of a phonocardiogram of a normal heart and the relevant Wavelet transform FIGS. 9 and 10 (from M.Vishwanath Shervegar, Ganesh.V.Bhat, Raghavendra M Shetty K. Phonocardiography—the future of cardiac Auscultation. International Journal of Scientific & Engineering Research Volume 2, Issue 10, October 2011, pp 1-12; http://www.ijser.org) are an example of a phonocardiogram from a heart subjected to heart failure and the relevant Wavelet transform.

Figure 11:
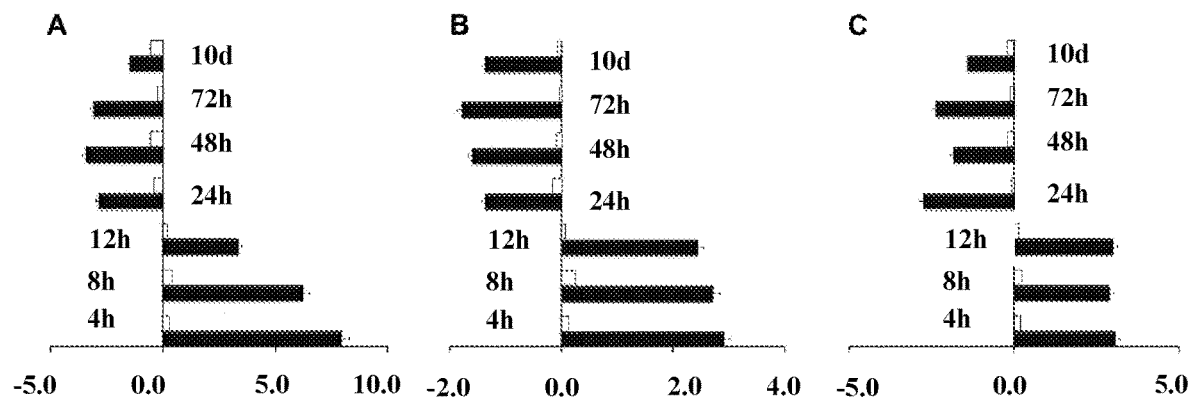
Figure 12:
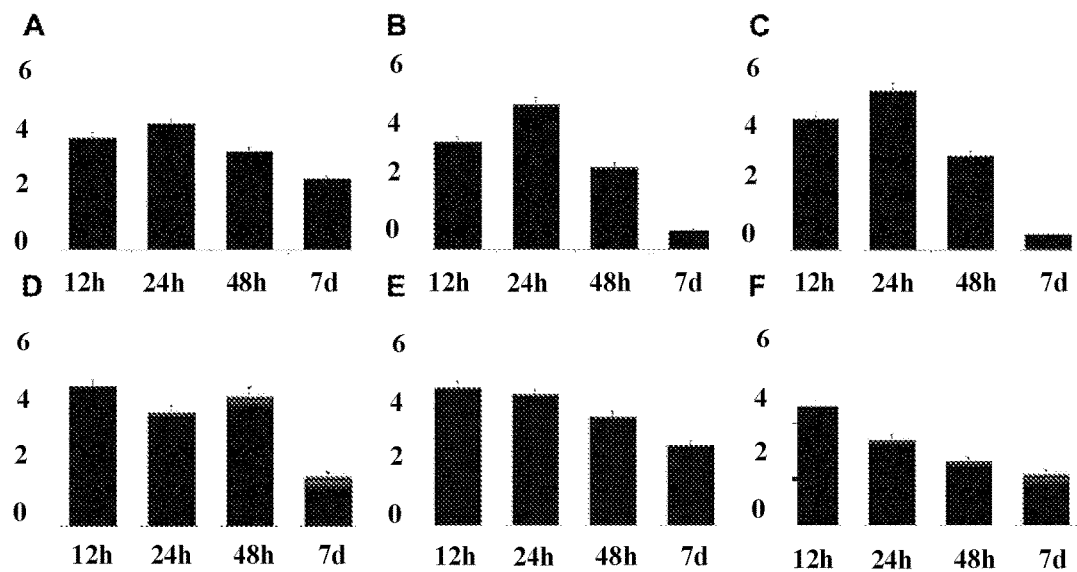

FIGS. 11 and 12 are examples of plots of the expression of genes in stem cells exposed to non-pathological and normal heart sounds according to the teaching of the present invention.

Figure 13:
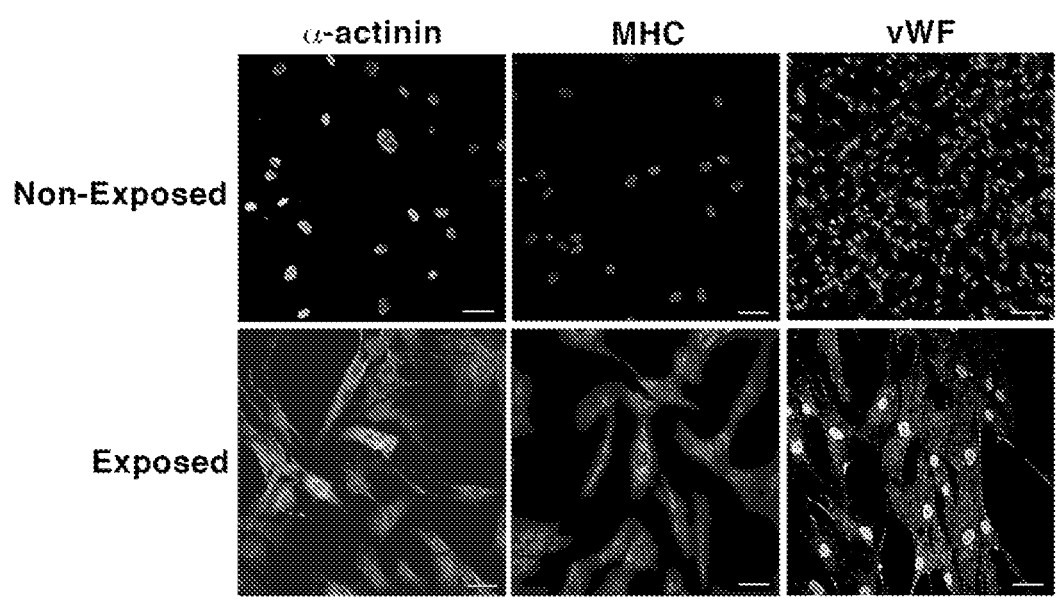

FIG. 13 is the results of another example obtained by exposing the stem cells to non-pathological heart sounds.

Since when the stethoscope has been invented in 1816, the auscultation of sounds emitted from the heart has been a practice widely used for the diagnosis of heart diseases. An instrument more evolved than the stethoscope is the phonocardiograph which allows noises occurring in a normal cardiac cycle to be graphically recorded.

The examination is carried out with the patient lying down with the naked chest in a room under the most complete silence and by placing the microphone on the several auscultatory areas; generally it is recorded together with other reference traces, such as for example the electrocardiogram. The normal phonocardiogram is composed of two groups of oscillations: the first one is composed of 4-6 uneven oscillations with a length of 100-140 ms corresponding to the first heart sound, the second one is composed of less wide oscillations with a length of 60 ms corresponding to the second heart sound.

The first sound is a vibration ranging from 5 to 100 Hz, caused by the almost contemporaneously closure of the mitral and tricuspid valves, at the beginning of the ventricular systole, while the second sound ranges from 50 to 150 Hz, it is generated by the closure of the pulmonary and aortic valves.

The first sound is followed by the short pause (corresponding to the ventricular systole), the second sound by the long pause (corresponding to the ventricular diastole). The first sound is always best recordable in the apex ausculatory area and it is composed of an initial group of low pitched and low amplitude vibrations, due to the myocardium being under tension. This is followed by the main vibrations of the first sound, high vibrations due to the closure of the atrium-ventricular valves with a high amplitude and a high pitch. The second sound is always best recordable in the base auscultatory areas and it is composed of two groups of high pitched and high amplitude vibrations (however always somewhat lower than those of the first sound), caused by the closure of the aortic and pulmonary valves.

Other two sounds, with a low pitch, and therefore slightly audible by the human ears, are the third and fourth sounds (in pathologic conditions they are called as ventricular gallop and atrial gallop respectively).

The third sound occurs about 200 ms after the second one, and it is caused by the rapid filling of the ventricle. It is typically audible in children and in individuals with a high cardiac output.

The fourth sound comes about 100 ms before the first one, and on the contrary it is generated by the atrial systole or presystole.

The main alterations that can be recorded by the phonocardiogram are the possible attenuation or intensification of heart sounds, their splitting and the occurrence of heart murmurs, of which it mainly allows their morphology to be defined, which is not always well audible by the simple auscultation. The morphology of heart murmurs is so important that often it allows the lesion to be exactly diagnosed.

Nowadays there are still apparatuses deriving from the old phonocardiographs, such as for example those called as Audicor by Inovise Medical Inc, Portland, USA, which are simply digital phonocardiographs, that is apparatuses able to record heart sounds and to process them by the use of evolved signal processing techniques. To this end see the article "Beyond auscultation—acoustic cardiography in the diagnosis and assessment of cardiac disease" by Paul Erne, Swiss Medical Weekly 2008; 138(31-32): 439-452.

Apart from the attempt made by the company Inovise as mentioned above for reawakening the concept of the direct auscultaton and of the relevant recording of heart sounds even if with evolved post-processing techniques, the phonocardiography, at least the conventional one, is now a technology considered out-of-date and widely replaced by the ultrasonography that is a diagnostic imaging technique that allows a complete visualization of the heart and of its functioning to be provided.

The operating principle shared by all the ultrasonography techniques is as follows: an ultrasound beam, generated from a transducer, is directed to the region to be examined and it is partially reflected by the discontinuous surfaces met along its path. The echo signal, received and detected generally by the same transducer, contains information about the reflectors that have originated it. Information about the distance of the reflector from the transducer is the most direct information and of immediate interpretation, which is obtained by measuring the delay between energy transmitted and received. More complex information is about the possible velocity of the reflector, related to the recognition of the frequency shift of the reflected wave due to the Doppler effect.

Consider a plane and infinite ultrasound wave with a frequency $f_0$ that meets along its path a moving obstacle with a velocity v. If the obstacle reflects the acoustic energy, the wave that goes back to the source has a frequency different from that of the incident wave by the amount:

$$f_d = \frac{2f_0}{c} v\cos\alpha$$

where c is the velocity of the propagation in the considered medium and α is the angle between the direction of the wave propagation and the velocity v. The frequency $f_d$ is called Doppler shift and it is directly proportional to the velocity component along the propagation direction of energy (v cos α).

Figure 1:
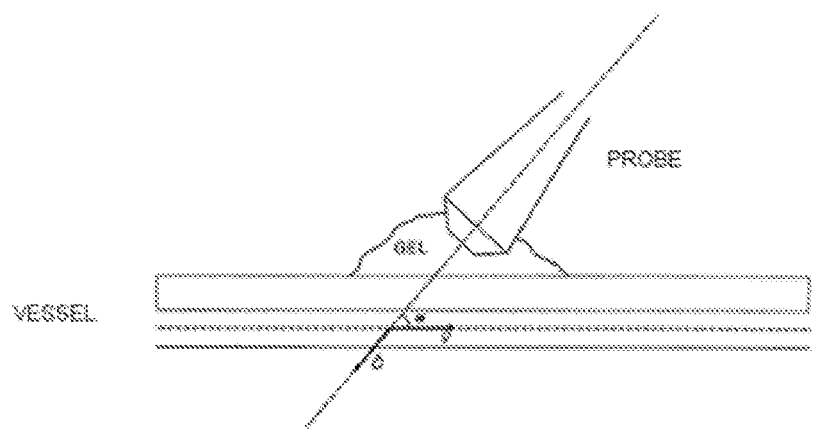
FIG. 1 is the operating principle of an ultrasonic Doppler flowmeter

The phenomenon described above is at the base of the operation of all the ultrasound apparatuses used for measuring in a non-invasive manner the blood flow for the diagnosis of cardiovascular diseases. FIG. 1 schematically shows the use of a simple Doppler flowmeter. A probe, upon which a piezoelectric transducer is fitted, is placed on the skin surface at the blood vessel or heart chamber to be examined. When the crystal is excited by a radiofrequency signal, it begins to vibrate, generating an ultrasound wave. A part of the energy transmitted is reflected by the structures present in the body to go back thereto or to a different transducer that converts it into an electric signal. Due to the motion of the particles in the blood and/or of the heart walls, the frequency of the return signal is different from that of the transmission by an amount $f_d$ that, by the equation above, directly provides an estimation of the velocity component of the particles in the pointing direction of the probe.

The ultrasound frequencies that are typically used range from 1 to 10 MHz. The maximum velocities measured in the arteries are in the range of 1 m/s with maximum values of 2-3 ms; since in the soft biological tissues the value of the propagation velocity c is about 1500 m/s, values of $f_d$ in the audiofrequency band (1-10 kHz) correspond to such velocities. From this the possibility of using such frequencies for generating sounds related to the cardiac activity.

To this end one embodiment of the invention provides the possibility of obtaining heart sounds to be delivered to stem cells by using a conventional ultrasound system, wherein Doppler frequencies are used for governing a dedicated sound processing chain for enhancing some frequencies with respect to other ones, for example by processing the signal in the frequency domain after sampling and subsequent FFT transform (Fast Fourier Transform) of the signal. The signals processed in this manner reach a speaker system that, in the most simple arrangement, is a loudspeaker, particularly a subwoofer in order to enhance low-pitched frequencies. The same processing system can be used for transferring to the speaker system the heart sound directly recorded by a microphone or a phonocardiograph. The processing of the signal obviously is not essential since the audio signal to be delivered to stem cells to be treated can be a simple repetition of the acquired one, possibly modified, without for this reason changing the content of the present invention.

In the simplest configuration the invention provides to record the sound on an analog medium such as a magnetic tape or a digital medium, such as a mass memory such as hard disk or flash memory, after sampling it, for example by using the sound card of a standard computer. The system that reproduces the sound to be sent to stem cells in this case can be separated from that used for acquiring it and it can also be independent therefrom. It is possible to provide an audio chain for the reproduction of digital samples which are anyway acquired once they have been stored on a mass storage device.

It is also possible to provide a dedicated device that comprises both an acquisition chain and a receiving chain both optimized for the application of the present invention.

Figure 2:
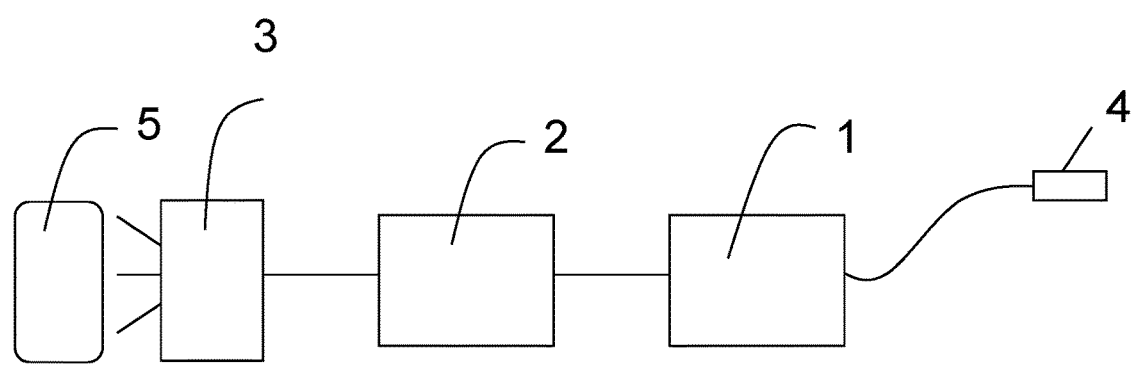
FIG. 2 is the block diagram of a device according to one embodiment of the invention.

FIG. 2 shows a block diagram of one embodiment of the invention. 1 denotes the heart sound acquisition chain while 2 denotes the chain providing to reproduce said sound after a possible processing. 3 denotes, as an example, a sound speaker element, such as for example a loudspeaker. The container with stem cells to be treated is denoted by 5.

In its simplest version, the chain 1 comprises one or more microphones 4 connected to a recorder or phonocardiograph, while in the most complex version it comprises an ultrasound device connected to a probe, that is a typical piezoelectric transducer, able to acquire heart signals, specifically heart sounds.

Figure 3:
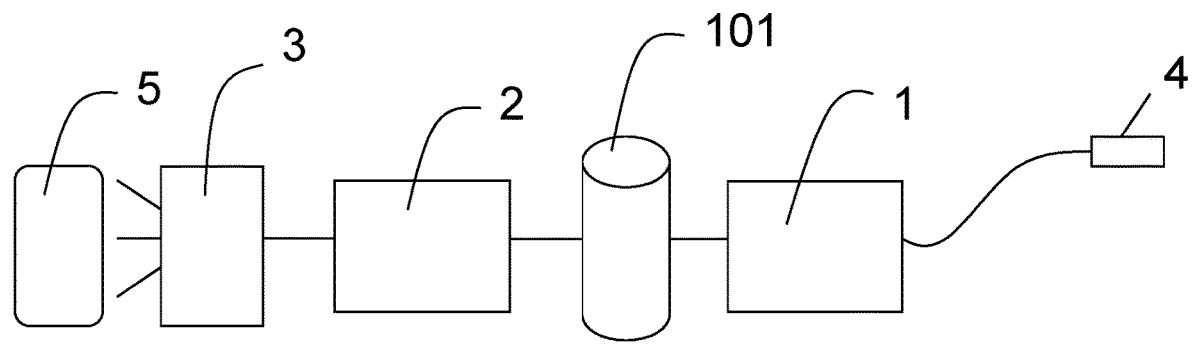
FIG. 3 is a variant of the device of the previous figure with a storage element interposed between the acquisition unit and the reproduction unit.

The output signals from the chain 1 can be both analog and digital depending on the type of acquisition chain 1 used. These signals can be stored or used in line by the reproduction chain 2. Since the stem cells will be subjected to heart sounds with a length higher than a cardiac cycle and after having acquired them, the most flexible solution is the possibility of storing the output sounds from the chain 1 such to use the same, or their samples, from the chain 2 for reproducing a duplicated or changed version of the sounds of interest for all the length of the treatment of the stem cells. This solution is depicted in FIG. 3 where 101 denotes a storage element such as a Hard Disk or a Flash Memory. Obviously any type of storage medium can be used too.

The chain 2 can even be summarized in a computer, or more generally in a microprocessor system, equipped with a sound card able to read from a memory the samples of the acquired sounds such to make a digital-analog reconstruction in sequence to be sent to the speaker 3. Due to the periodicity of the signal, it will be sufficient to acquire even only one cardiac cycle and to repeat it for all the length of the treatment. Generally several cardiac cycles will be necessary for detecting possible alterations thereof over time that can affect the change in the potency of the stem cells to be treated.

The reproduction chain 2 can comprise an amplifier and one or more filters for extracting frequencies considered to be the most significant for each application. For example it is possible to provide to enhance frequencies below 50 Hz by using a subwoofer as the sound speaker 3 or to select frequencies corresponding to one of the four heart sounds described above such to send in sequence sounds with a different frequency content and for different times depending on the type of treatment to be carried out.

As regards the modes for carrying out the exposure of cells to sound waves generated by the device of the invention, several solutions are possible from the most simple that provides to use a loudspeaker, particularly a subwoofer, placed near the container wherein the cells to be treated are provided, to the most complex ones that provide to integrate the speaker inside the container for better transmitting the sound.

Stem cells to be treated can be for example obtained by any method such as for example described in patent applications US2007/0274960, WO2011/145075, WO2003/085099. The soundproofing step can be performed during the whole time interval or only in a part thereof as well as in a subsequent or preceding step without for this reason changing the content of the present invention.

According to one embodiment, the container wherein the stem cells to be treated are provided is the one used in the device for preparing the transplantation adipose tissue described in the international patent application published under the number WO2011/145075. In practice it is a container made of plastic or sterile glass, or anyway a translucid material, preferably resistant to high temperatures and autoclavable, inside which the liposuctioned adipose material is injected.

Figure 4:
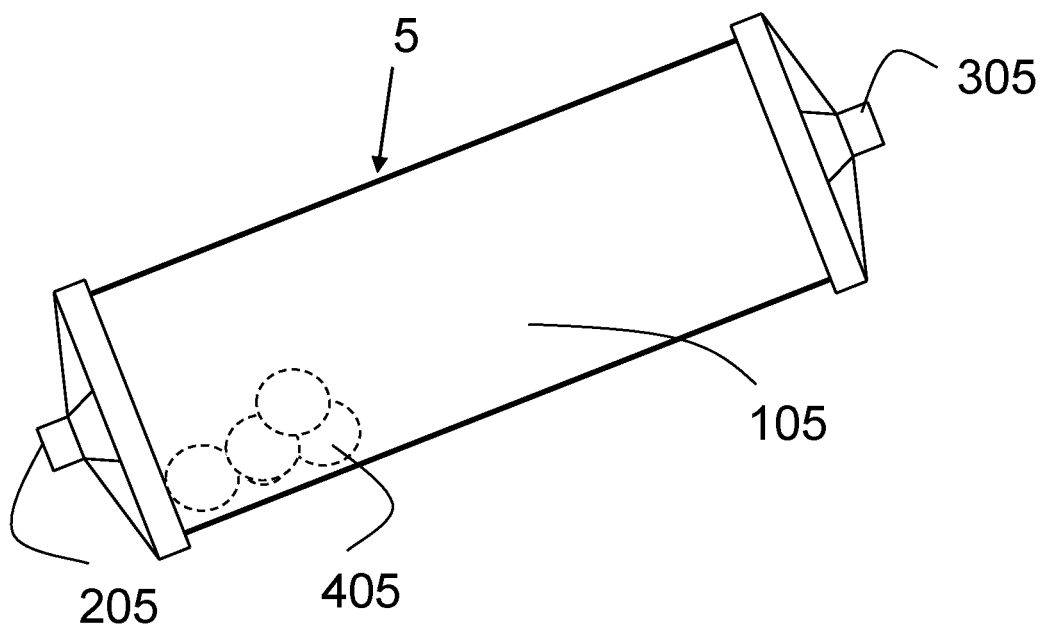
FIG. 4 is an example of a known device that can be used for extracting stem cells to be treated according to the process of the present invention.

Such as shown in FIG. 4 the container 5 is provided with a washing chamber 105 for the liposuctioned material which container 5 has an inlet 205 and an outlet 305 such that the liposuctioned material can enter through the inlet 205 in the washing chamber 105 and from said chamber 105 at least a part of said material, particularly in order of time, firstly the fluid component and then the solid component, can exit through the outlet 305, inside said washing chamber 105 there being provided means for mechanically generating an emulsion of the fluid components, particularly of the oil obtained by breaking the adipocytes, blood and/or other sterile liquid solutions.

Said emulsion generating means are composed of at least one stirring element 405, such as balls or the like, of equal or different sizes, for increasing emulsion of liquid components when the container 5 is subjected to stirring. In the device the simple manual stirring of the device is enough for obtaining the separation of the liquid phase composed of the fluid emulsion from the solid phase composed of cells, cell fragments, cell aggregates.

The possible reduction of cell aggregates by the use of filtering meshes allows small cell agglomerates to be provided, particularly microagglomerates of fat cells or individual cells, having stems cells adhered on their outer surface which can be subjected to mechanical vibrations induced by the diffuser during the whole process separating the liquid part or a part thereof or also, or only, later in the same or in another container possibly in a culture suitably arranged for extracting stem cells.

Thus it is possible to obtain not only fat material to be used as a biological filler, but also material rich in pluripotent stem cells, or at least with an enriched potency or anyway a modified potency, that can be used for regenerating tissues even different than those from which said material has been extracted.

Now an example of a mode for acquiring and reproducing heart sounds to be delivered to stem cells according to the present invention is described.

Hardware and software used for the acquisition are as follows:

1. E Scope® electronic stethoscope by Cardionics, Webster, Tex. modified to record signals below 20 Hz. The frequency range for the E-Scope is 5-900 Hz.
2. Digi 002 Pro Tools workstation with software version 7.1 from Digidesign for digital recording of heart sounds.
3. PCI 6052E 333KS/s acquisition card with LabView 8 software from National Instruments.
4. NI (PCI) 4551 signal analyzer from National Instruments.
5. Connector blocks for 2120 (PCI 6052E) and 2140 (NI4551).
6. DataLab 2000 with software version 1.4.5 from Lafayette Instrument for interface with ECG, EEG, EMG and other physiological signals.
7. K2 power (500-1600 W) amplifier from Crown.
8. Mac-OS 10.4 (Pro Tools) interfaced by shielded cables and connector block 2120 with LabView on Windows XP.

As regards the signal processing, this is divided into 3 sections:

1. Waveform conditioning: heart sounds are filtered using a IIR filter to remove noise, in particular to remove noises due to breathing when acquiring low pitch sounds.

2. Waveform measurements: to precisely reconstruct a waveform starting from its digital samples it is necessary to observe the so called Nyquist limit that dictates the acquisition of a signal that is at least twice its maximum frequency (Shannon theorem). In this step it is verified whether said limit is observed.

3. Waveform monitoring: this step includes finding the peaks and valleys of the signal. The maximum differential value between adjacent peaks provides a duration to each heart sound to be converted into a music sound.

The above three processing sections provide the framework for developing a series of algorithms among which we can mention:

1. The main algorithm: each heart sound is analyzed for their frequency (pitch), amplitude, and offset to generate a corresponding music sound to be submitted to stem cells to be treated.
2. Sub-algorithm to change the number of samples
3. Sub-algorithm to change the frequency (pitch) of discrete parts of the waveform below 50 or above 90 beats per minute.
4. Sub-algorithm that updates and converts the sample signal into a music sound.
5. Sub-algorithm that divides the waveform into 8 and 12 time subdivisions relative to the changing duration of each heart cycle. It has to be noted how amplitude changes occurring close to time values that are a fractional part of the waveform based on 12 subdivisions, will produce greater compliancy of cardiac muscle activity.

As regards the generation of the output signal (E-MAS Electro-Music Audio Signal), this can be summarized in the following steps.

1. Designing a Virtual Instrument in LabView. LabView is a programming language that uses graphics in place of code. The two major windows of LabView are called the Front Panel (that is the musical instrument) and the Block Diagram (that is the components inside the instrument).

In particular the Front Panel is the interface to the source code in the Block Diagram. It contains controls (inputs) that simulate knobs and switches that are usually provided on a physical instrument and indicators (outputs) that display the data in various graphic forms.

The Block Diagram is where the source code is located. The objects in the Block Diagram can be organized into three groups:

a) Nodes that execute arithmetical and writing functions;
b) Terminals that allow data to flow between the Block Diagram and the Front Panel;
c) Wires that transmit data between terminals.

The process of designing the virtual instrument for converting heart sounds into music sounds requires solving the problem of how to deal with time events occurring in a short period of time (i.e., sampling period) while maintaining the integrity of the signal that has been sampled. This was solved by developing a suitable multitasking/multithreading framework with a specific coordination of synchronous and asynchronous functions of LabView to manage the high variability and unpredictability of bio-signals that are acquired.

To assign a variable time function (i.e., duration) to a variability in frequency domain, the Shift Register of LabView has been used which is particularly useful for managing the synchronization among the different functions in the virtual instrument.

2. Designing an algorithm to compromise with the uncertainty principle of sampling at small intervals of time and its effect on relative frequency changes. When measuring the sound frequency, the accuracy of the measurement is relative to the length of the sampling time. The lesser the measuring interval (number of samples per period of time) is, particularly with respect to time of 1 s that is the standard time interval for measuring frequencies, the greater the measurement error that will be encountered. The frequency (pitch) and duration are two important parameters that affect the conversion of a heart sound into a music sound. The time component of the music sound is derived from the time difference between two peak points in the waveform. However, sampling periods that were approximately 90% below the sample rate produce a waveform with less than two peak points. To resolve this issue an algorithm was designed to measure the length of the fractal part of the waveform that is less than the time between two subsequent peak points such to use such length as the total duration of the component of the music sound. Further adjustments of the algorithm include increasing or decreasing the octave level of the pitch relative to the duration of the fractal component.

| Frequency # | Frequency (Hz) | Duration (ms) |
| --- | --- | --- |
| F1 | 53.52 | 209 |
| F2 | 40.80 | 91 |
| F3 | 95.20 | 422 |
| F4 | 104.90 | 235 |
| F5 | 51.42 | 445 |
| F6 | 51.25 | 565 |
| F7 | 50.79 | 904 |
| F8 | 53.51 | 861 |

The table reports, by way of example, the frequencies obtained by using the above reported method. The overall pattern of frequencies was recorded from normal hearts without abnormalities in the echocardiographic analysis. In particular, the dimensions of the heart chambers (right and left atria and ventricles), the left ventricular thickness (anterior and posterior wall), the left ventricular end-systolic and end-diastolic diameters, the ejection fraction %, the cardiac output, the stroke volume were all within the normal range. Moreover, no arrhythmias were recorded.

On the whole, the cardiac cycle of phonocardiogram (PCG) is characterized by transients and fast changes in frequency as time progresses. It has been shown that basic frequency content of PCG signal can be easily provided using a FFT (Fast Fourier transform) technique. However, time duration and transients cannot be resolved by this technique. To analyze signals having these characteristics the wavelet transform (continuous or discrete version) is the most suitable technique. It was also shown that the coefficients of the continuous wavelet transform can be used for giving a graphic representation that provides a quantitative analysis simultaneously in time and frequency domain making this type of transform very helpful in extracting clinical information. To this aim see Ult P et al. "Detection of the third heart sound using a tailored wavelet approach", Med Biol Eng Comput. 2004 March; 42(2):253-8 and Meziani F et al. "Analysis of phonocardiogram signals using wavelet transform", J Med Eng Technol. 2012 August; 36(6):283-302. doi: 10.3109/03091902.2012.684830. Epub 2012 Jun. 28.

Figure 5:
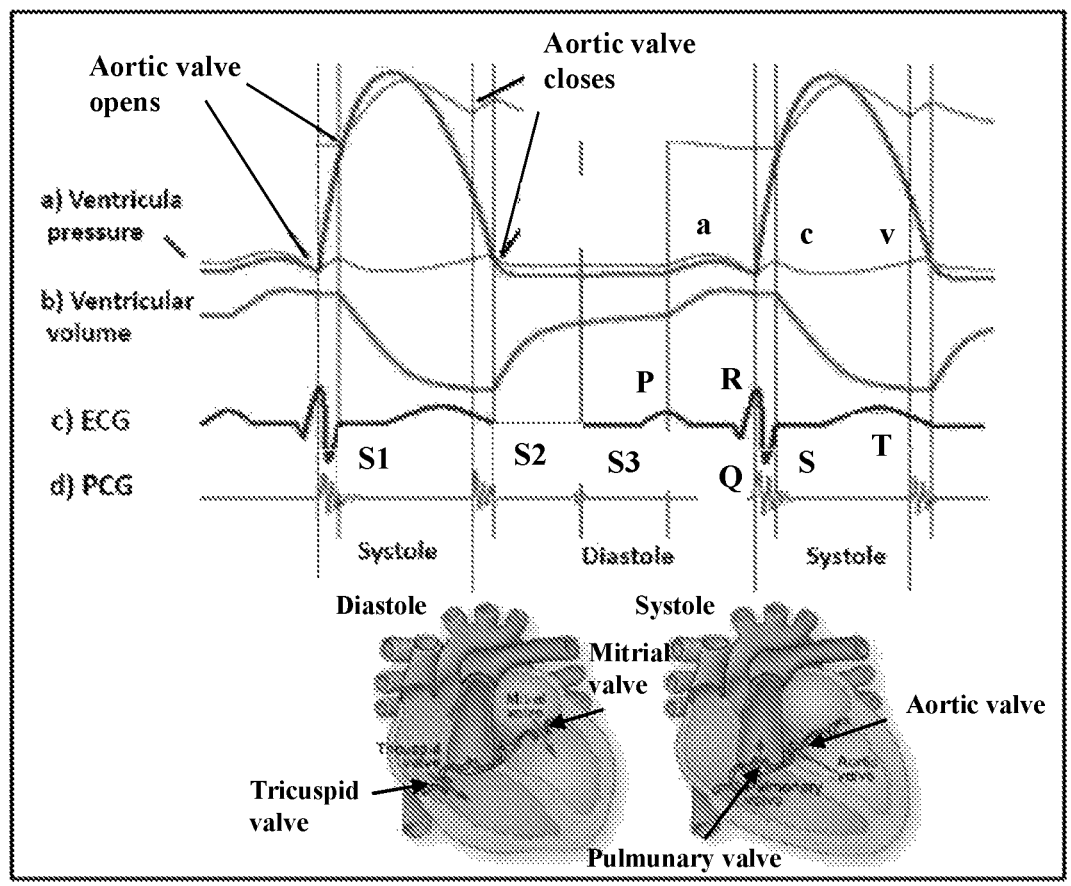
FIG. 5 is the plot of such parameters Ventricular pressure (a), Ventricular volume (b), ECG trace (c), phonocardiogram trace (d) within one heart cycle.

Within this context, it has to be noted how the third heart sound is normally heard during auscultation of younger individuals, but disappears with increasing age. However, this sound can appear in patients with heart failure and is thus of potential diagnostic use. As shown by the above mentioned publication by Ult P et al., it is possible to acquire phonocardiograms from healthy children, all known to have a third heart sound, to provide knowledge about the features of said sound in a non-pathologic field. Using this knowledge, a wavelet procedure has been developed to identify said sound that was shown to be superior to what can be obtained by FFT transform. This method was applied to phonocardiograms from patients known to have heart failure. The method was able to detect third heart sounds effectively (90%), with a low false detection rate of 3.7%, which supports its clinical use. The method was capable of detecting, not only distinct and clearly visible third heart sounds in children, but also in adult pathologic patients. FIG. 5 shows some examples of normal and pathological phonocardiogram traces.

The two major audible sounds in a normal cardiac cycle are the first (S1) and the second (S2) heart sound, as depicted in the figure:

S1 occurs at the onset of the ventricular contraction during the closure of the AV valves. The S1 sound contains a series of low-frequency vibrations, and it is usually the longest and loudest component of the PCG signal. The audible sub-components of S1 are those associated with the closure of each of the two AV-valves. S1 lasts for an average period of 100-200 ms and its frequency components lie in the range of 25-45 Hz. It is usually a single component, but may be also split with some pathologies.

S2 is heard at the end of the ventricular systole, during the closure of the semilunar valves. It lasts about 0.12 s, with a frequency of 50 Hz which is typically higher and shorter in terms of duration with respect to S1. S2 has aortic components A2 and pulmonary sub-components P2. Usually A2 and P2 are close together, but a split of S2 can occur if A2 and P2 are just far enough apart that they can be heard as two beats within S2.

S3 is the third low-frequency sound that may be heard at the beginning of the diastole, during the rapid filling of the ventricles. Its occurrence can be normal in young people (less than 35 years of age). It has been shown to be highly representative for a diseased heart failing condition in elder subjects.

S4 is the fourth heart sound that may occur in late diastole during atrial contraction shortly before S1. It is always considered as an abnormality within the cardiac cycle.

Click and Snaps are associated with valves opening and indicate abnormalities and heart defects. Opening snaps of the mitral valve or ejection sound of the blood in the aorta may be heard in case of valve disease (stenosis, regurgitation). The most common click is a systolic ejection click, which occurs shortly after S1 with the opening of the semilunar valves. The snap when present, occurs shortly after S2 with the opening of the mitral valve and tricuspid valve.

Murmurs are high-frequency, noise-like sounds that are heard between the two major heart sounds during systole or diastole. They are caused by turbulence in the blood flow through narrow valves or reflow through the atrioventricular valves due to congenital or acquired defects. They can be innocent, but can also indicate certain cardiovascular defects.

Figure 6:
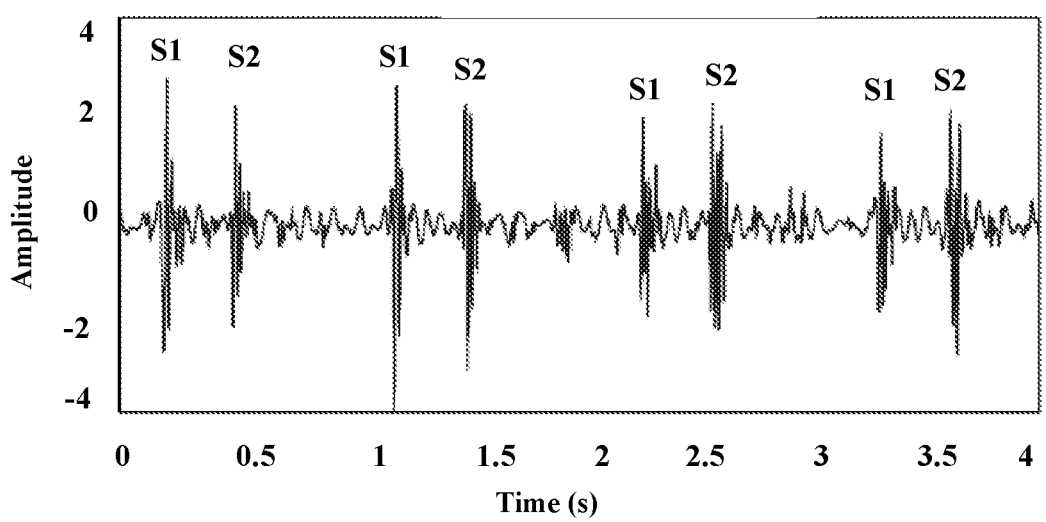
FIG. 6 is the different components of a normal phonocardiogram.
Figure 9:
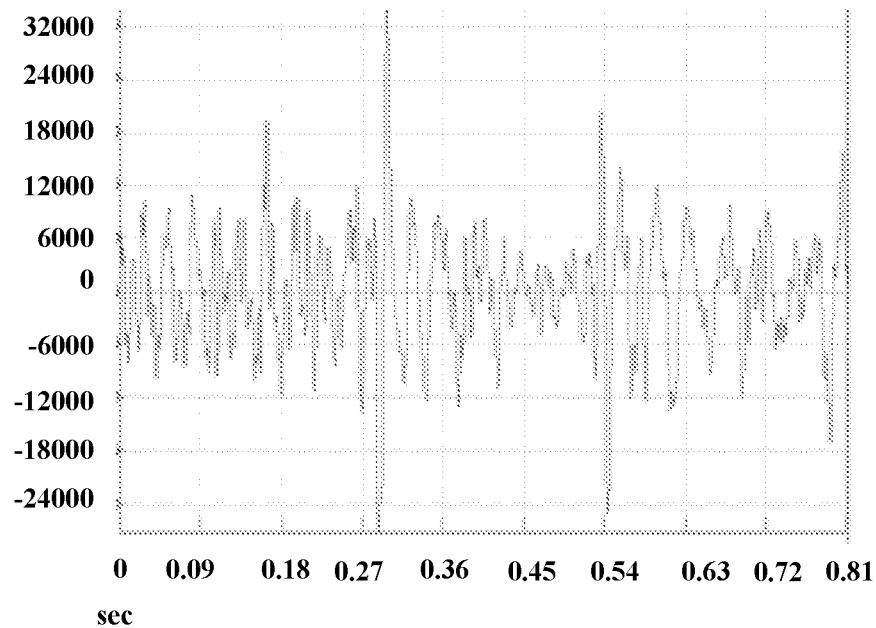
Figure 10:
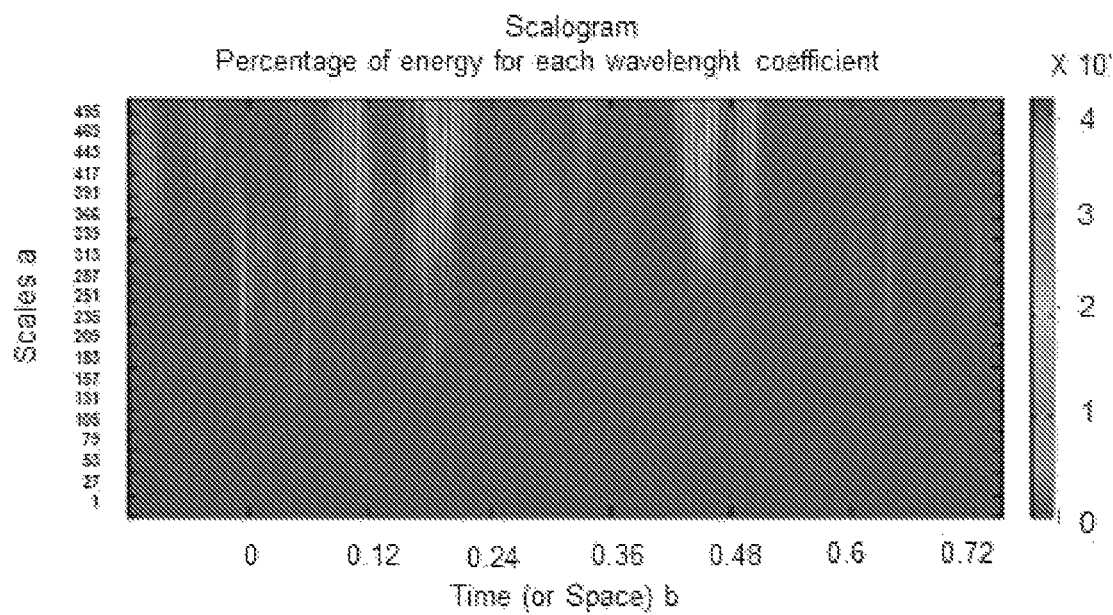

FIGS. 6 and 8 show an example of a phonocardiogram of a normal and abnormal heart, respectively. FIGS. 7 and 9 show Wavelet transforms of said phonocardiograms.

Now an example of the system for the exposure of stem cells to a heart sound according to the present invention and the results obtained by it are described.

Stem cells within their culture liquid were placed onto a mechanical transducer composed of a loop coil containing a mass in suspension, transforming the signal applied thereto into a linear oscillating movement. The system also includes a resistive load to fit the load to the amplifier, a final power amplifier that controls the level of the signal applied to the transducer, an equalizer comprising 30 frequency regulators for adjusting the sound spectrum from 0 to 20 kHz, a mixer allowing the amplification of signals of mV up to V.

The signal, from a PC equipped with a high performance sound card, comes to the mixer, which by the aid of adjustable level knobs brings the weak signal outputted from the PC up to a suitable level for the equalizer. The latter, by the aid of the 30 frequency regulators, provides to equalize the outgoing signal in order to make the transducer response as linear as possible.

Now some experimental results obtained by the above system are shown.

Effects of the Heart Sound on Stem Cell Homeostasis and Commitment

As it can be noted in FIG. 11, human stem cell exposure to the normal heart sound early enhances the expression of stemness related genes, such as Nanog, Sox2, and Oct4, within the first 2-4 hours, with an up-regulation persisting up to 12 hours, followed by a downregulation below the control level during the subsequent hours and days.

On the contrary, stem cell exposure to the heart sound recorded from patients with heart failure of different origin, such as previous myocardial infarction, dilating cardiomyopathy, atrial, ventricular septal or valvular defects, had no significant effect on the transcription of the above mentioned genes.

Such FIG. 11 shows how the exposure to the normal heart sound modulates the expression of sternness related genes.

Human adipose-derived stem cells were exposed for the indicated times to the sounds recorded from normal (black bars) or diseased hearts (white bars). A, Sox2, B, Oct4, C, Nanog.

The amount of each transcript expressed from exposed cells in the absence or presence of the sound (from normal or abnormal heart) was normalized with respect to the expression level of HPRT1 gene (hypoxanthine phosphoribosyltransferase 1), and the mRNA expression of sound exposed cells was plotted, at each time point, as change (number of times) relative to the expression value in control unexposed cells, defined as 1 (mean±Standard Error; n=6).

How it can be seen in FIG. 12 the effects produced by a normal heart sound on sternness genes are associated with a significant increase in the expression both of cardiogenic genes, such as prodynorphin, Nkx-2.5, and GATA-4, and vasculogenic genes, such as VEGF (vascular endothelial growth factor), HGF (hepatocyte growth factor), and vWF (von Willebrand factor).

FIG. 12 shows how the exposure to the normal heart sound enhances the expression of cardiogenic and vasculogenic genes.

Human adipose-derived stem cells were exposed for the indicated times in the absence or presence of the sounds recorded from normal hearts.

The amounts of prodynorphin (A), Nkx-2.5 (B), GATA-4 (C), VEGF (D), HGF (E), vWF (F) mRNA from exposed cells in the absence or presence of normal heart sound were normalized relative to the expression level of HPRT1 (hypoxanthine phosphoribosyltransferase 1) gene, and the expression of each mRNA in sound exposed cells was plotted, at each time point, as change (number of times) relative to the expression value in control unexposed cells, defined as 1 (mean±Standard Error; n=6).

All the data from exposed cells at each time point were significantly different from control unexposed cells (mean±S.E.; n=6; $P<0.05$).

Stem cell exposure to the sounds recorded from diseased hearts (3 patients with post-infarct heart failure, 3 patients with dilating cardiomyopathy) was ineffective in modifying the mRNA levels detected in control unexposed cells (not shown).

The observed changes in the amount of each transcript were mirrored at similar changes in the levels of expression of the corresponding proteins.

No transcriptional response was found after stem cell exposure to the sounds recorded from diseased hearts.

Confocal microscopy analysis provided evidence that stem cell exposure to the heart sound of normal subjects led to a remarkable increase in the expression of cardiac markers, such as α-myosin heavy chain, α-sarcometic actinin such as shown in FIG. 13.

Such figure shows how the exposure of stem cells to the normal heart sound drives the differentiation towards miocardial and vascular phenotypes.

The expression of α-sarcomeric actinin (α-actinin), α-myosin heavy chain (MHC), and (vWF) was assessed in cells cultured for 7 days in the absence or presence of the normal heart sound. Nuclei are labeled with DAPI (blue).

Scale bars are 40 micron.

Images are representative of six separate experiments. For each tissue differentiation marker, fields with the highest yield of positively stained cells are shown.

The treatment with the normal heart sound has further led to a consistent increase in the yield of cells positively stained for specific marker proteins of mature endothelial cell differentiation, including vWF.

No evident commitment was observed following the exposure to the sound of diseased hearts (3 patients with post-infarct heart failure, 3 patients with dilating cardiomyopathy).

Therefore the expression of both sternness and cardiogenic/vasculogenic genes is specifically modulated by subjecting the cells to a normal heart sound, since the sounds recorded by the hearts affected by a wide range of diseases are ineffective.

Obviously the invention is not limited to the embodiments described and shown above, but it can be widely changed, above all from a structural point of view. For example it is possible to provide to use the device according to the invention for inducing vibrations to stem cells not only inside a container, particularly in a culture, but also in vivo that is directly on the patient to be treated such to change the potency thereof already in the tissue where they are provided for being possibly subsequently taken out or for being directly used in situ. In this case the speaker element of the device will be directly applied on the skin of the patient near the area to be treated. Moreover it is possible to provide to treat also other types of cells such as for example adult somatic cells, even human ones, non-stem cells such as fibroblasts or non human embryonic cells to obtain a kind of programming of the potency thereof. All this without departing from the teaching principle disclosed above and claimed below.

REFERENCES

Huang C H, et al. J Cell Biochem 108:1263-1273, 2009
Doyle A M, et al. Ann Biomed Eng 37:783-793, 2009

Wolf C B, et al. in Trends in stem cell biology and technology. Baharvand H, ed. Humana Press, 2009; pp 389-403
Higuchi T, et al. J Nucl Med 50:1088-1094, 2009
Vajkoczy P, et al. J Exp Med 197: 1755-1765, 2003
Aicher A, et al. Circulation 114:2823-2830, 2006
Lionetti V, et al. J Biol Chem 285:9949-9961, 2010
Hu B S, et al. Am J Physiol Heart Circ Physiol 293:H677-H683, 2007
Ventura C, et al. FASEB J 19:155-157, 2005
Maioli M, et al. Cell Transplant 2011; September 22.doi: 10.3727/096368911X600966
Abrams G A, et al. Cell Tissue Res 299:39-46, 2000

The invention claimed is:

1. A process for inducing the expression of stem cell markers in the cells of a lipoaspirate, said process comprising the steps of:
   providing a lipoaspirate obtained by a non-enzymatic minimal manipulation procedure; and
   exposing, for at least four hours, said lipoaspirate to vibrations derived from a heart sound by ultrasonography examination by extracting a Doppler signal from echoes of ultrasound waves received by soundproofing with a heart probe, or a part thereof, or a blood vessel, wherein the signal is processed by
   1) filtering heart sounds using an IIR filter to remove noise;
   2) reconstructing a waveform starting from its digital samples and verifying that the Nyquist limit, the limit that dictates the acquisition of a signal, is at least twice its maximum frequency; and
   3) finding the peaks and valleys of the signal, wherein the maximum differential value between adjacent peaks provides a duration to each heart sound to be converted into a music sound, and wherein said vibrations have frequencies ranging from 1 to 10 MHz,
   wherein the stem cell markers include at least one of Sox2, Oct4, and Nanog.

2. The method according to claim 1, wherein said lipoaspirate comprises lobular fat material.

3. The method according to claim 2, wherein said lobular fat material comprises a fluid component having an oil component, an hematic component or a sterile solution; and a solid component comprising vascular-stromal structures comprising pericytes or mesenchymal stem cells, cell fragments or one or more cell macroagglomerates of heterogeneous size and comprising stem cells.

4. The method according to claim 3, wherein said fat material is divided into cell agglomerates with a smaller size than the size of said macroagglomerates so that said cell and/or vascular-stromal agglomerates have a size equal to or smaller than a predetermined value, and so that said sizes are, on average, equal to one another.

5. The method according to claim 1, wherein the lipoaspirate comprises human adult stem cells or non-stem somatic adult cells.

* * * * *